(12) United States Patent
Kim et al.

(10) Patent No.: US 9,498,299 B2
(45) Date of Patent: Nov. 22, 2016

(54) PRECISE PLACEMENT DEVICE FOR PRECISE INSERTION OF INSERT

(75) Inventors: Keehoon Kim, Seoul (KR); Sinjung Kim, Andong-si (KR); Sang Rok Oh, Seoul (KR)

(73) Assignee: KOREA INSTITUTE OF SCIENCE AND TECHNOLOGY, Seoul (KR)

(*) Notice: Subject to any disclaimer, the term of this patent is extended or adjusted under 35 U.S.C. 154(b) by 728 days.

(21) Appl. No.: 13/617,580

(22) Filed: Sep. 14, 2012

(65) Prior Publication Data

US 2013/0079799 A1 Mar. 28, 2013

(30) Foreign Application Priority Data

Sep. 26, 2011 (KR) .................. 10-2011-0096828

(51) Int. Cl.
 *A61B 19/00* (2006.01)
(52) U.S. Cl.
 CPC .................................... *A61B 90/11* (2016.02)
(58) Field of Classification Search
 CPC ... A61B 17/20; A61B 17/22; A61B 17/5244
 See application file for complete search history.

(56) References Cited

U.S. PATENT DOCUMENTS

| | | | | |
|---|---|---|---|---|
| 5,004,457 A | * | 4/1991 | Wyatt et al. | 604/158 |
| 5,441,505 A | * | 8/1995 | Nakamura | 606/130 |
| 5,601,569 A | * | 2/1997 | Pisharodi | 606/130 |
| 5,787,886 A | * | 8/1998 | Kelly et al. | 600/407 |
| 5,964,715 A | * | 10/1999 | Thunberg | 600/562 |
| 6,409,735 B1 | * | 6/2002 | Andre et al. | 606/130 |
| 7,212,609 B2 | * | 5/2007 | Nagamine e | 378/65 |
| 8,038,108 B2 | * | 10/2011 | Yasunaga et al. | 248/123.2 |
| 8,551,108 B2 | * | 10/2013 | Pelletier | A61B 19/5244 606/102 |
| 2007/0250078 A1 | * | 10/2007 | Stuart | 606/130 |
| 2008/0058837 A1 | * | 3/2008 | Steinberg | 606/130 |
| 2009/0056021 A1 | * | 3/2009 | Kuro et al. | 5/601 |
| 2009/0248044 A1 | * | 10/2009 | Amiot et al. | 606/130 |
| 2010/0234856 A1 | * | 9/2010 | Stoianovici et al. | 606/130 |

FOREIGN PATENT DOCUMENTS

KR 1020000061358 * 4/2002 ............... A61B 6/04

OTHER PUBLICATIONS

Description of Instruments for stereotactic surgery developed by David-Kopf Instruments of USA (13 pp, in English), <Web URL: http://www.kopfinstruments.com>, Sep. 19, 2011.

* cited by examiner

*Primary Examiner* — Julie A Szpira

(57) ABSTRACT

The precise placement device includes: a direction controller to which a placement unit having an insert and a drill is mounted, the direction controller controlling a direction of the placement unit; a precise transfer unit to which the direction controller is mounted, the precise transfer unit transferring the placement unit in the planar two-axis direction; a support table for fixing a target for insertion in which the insert is to be placed; and transfer units for transferring the precise transfer unit and the operating table.

15 Claims, 11 Drawing Sheets

PRECISE PLACEMENT DEVICE FOR PRECISE INSERTION OF INSERT

CROSS-REFERENCE TO RELATED APPLICATION

This application claims priority to Korean Patent Application No. 10-2011-0096828, filed on Sep. 26, 2011, and all the benefits accruing therefrom under 35 U.S.C. §119, the contents of which in its entirety are herein incorporated by reference.

BACKGROUND

1. Field

The present disclosure relates to a placement device for inserting an insert into a target, and more particularly, to a precise placement device for precise insertion of a small insert.

2. Description of the Related Art

A precise placement device which allows precise insertion of a small insert such as an electrode is indispensable for brain surgery or the like.

Brain surgery is one of most sensitive and difficult surgeries in the neurosurgery, and the stereotactic surgery is the essence of the brain surgery.

The stereotactic surgery is performed by forming a minute hole in the brain in a state where the position coordinate of the head and the coordinate of a surgery device are aligned to agree with each other by mutual compensation.

As described above, in order to perform the stereotactic surgery, the accuracy should be ensured by performing the stereotactic surgery to a small animal (generally corresponding to a rat).

An electrode placement device for stereotactic surgery, which has been developed by DAVID-KOPF Instrument of USA, fixes the head of a rat, incises the scalp, and then positions a drill above a point that the user intends to perforate by manipulating the electrode placement device. Then, the drill is moved downwards to perforate the cranial bone of the rat.

The electrode placement device configured as above may perforate only in the vertical direction even though the drill moves 3-dimensionally till the drill is positioned at the perforation point, because the drill moves downwards in a state where the drill is positioned vertically at a point above the perforation point. And, the electrode may also be placed only in the vertical direction through the perforated hole.

Therefore, in a case where a dangerous tissue is located above the nerve nucleus where the electrode is to be placed, it is impossible to insert the electrode. In addition, in a case where multiple electrodes should be inserted into a single nerve nucleus, the surgery is substantially impossible if the convention electrode placement device is used.

SUMMARY

The present disclosure is directed to solving the problems of the conventional art as described above and providing a precise placement device which allows a small insert such as an electrode to be precisely inserted into a target.

The present disclosure is also directed to providing a precise placement device which allows rapid positioning of a terminal to which a drill and an insert are mounted.

In one aspect, there is provided a precise placement device, which includes: a direction controller to which a placement unit having a drill and an insert is mounted, the direction controller controlling a direction of the placement unit; a precise transfer unit to which the direction controller is mounted, the precise transfer unit transferring the placement unit in the planar two-axis direction; a support table for fixing a target for insertion in which the insert is to be placed; and transfer units for transferring the precise transfer unit and the support table.

According to an embodiment of the present disclosure, the transfer units may include: a vertical transfer unit to which the precise transfer unit is mounted, the vertical transfer unit transferring the precise transfer unit in a vertical direction; and a planar transfer unit for transferring the support table in planar two-axis directions.

According to an embodiment of the present disclosure, the planar transfer unit may include two transfer units mounted to a base and relatively moving in two-axis directions orthogonal to each other, and the support table may be movable in the two-axis directions by means of the two transfer units.

According to an embodiment of the present disclosure, the planar transfer unit may include an X-axis transfer portion for transferring a support table in an X-axis direction which is one of the two axes and a Y-axis transfer portion mounted to the X-axis transfer portion to transfer the support table in a Y-axis direction, the X-axis transfer portion may include a frame fixed to the base, a shaft fixed to the frame in the X-axis direction, and a linear motor moving along the shaft, the Y-axis transfer portion may include a frame mounted to the linear motor of the X-axis transfer portion, a shaft fixed to the frame in the Y-axis direction, and a linear motor moving along the shaft, and the support table may be fixed to the linear motor of the Y-axis transfer portion.

According to an embodiment of the present disclosure, the vertical transfer unit may include a frame perpendicularly fixed to a base, a shaft fixed to the frame in a Z-axis direction which is a vertical direction, and a linear motor moving along the shaft, and the precise transfer unit may be mounted to the linear motor.

According to an embodiment of the present disclosure, the precise transfer unit may include two plates mounted to the vertical transfer unit to relatively move in two-axis directions orthogonal to each other, and first motors linked to the two plates, respectively, to relatively move the plates in directions orthogonal to each other.

According to an embodiment of the present disclosure, two first motors may be mounted to a bracket fixed to the vertical transfer unit, one end of a first link may be fixed to a rotary shaft of each of the two first motors, one end of a second link may be hinged to the other end of the first link, and the other end of the second link may be hinged to the plate.

According to an embodiment of the present disclosure, a first fixed plate having a protrusion in one of the two axes may be fixed to a bracket horizontally fixed to the vertical transfer unit, a first plate matched with the protrusion to move along the protrusion may be mounted to the upper surface of the first fixed plate, a second fixed plate having a protrusion in the other of the two axes may be fixed to the upper surface of the first plate, a second plate matched with the protrusion of the second fixed plate to move along the protrusion may be mounted to the upper surface of the second fixed plate, and the link and the direction controller may be mounted to the second plate.

According to an embodiment of the present disclosure, a bracket may be fixed to one side of the second plate so that the link is hinged to the bracket, and a fixed board may be fixed to the other end of the second plate so that the direction controller is mounted to a terminal of the fixed board.

According to an embodiment of the present disclosure, the direction controller may include a second motor mounted to the precise transfer unit, a bracket fixed to a rotary shaft (roll shaft) of the second motor to rotate based on the rotary shaft of the second motor, and a third motor fixed to the bracket, and the placement unit may be fixed to a rotary shaft (pitch shaft) of the third motor to rotate based on the rotary shaft of the third motor, the placement unit being rotatable based on the rotary shaft (roll shaft) of the second motor.

According to an embodiment of the present disclosure, the placement unit may include a placement portion having one end to which the drill is mounted and the other end to which the insert is mounted, a holder having a hollow through which the placement portion passes and fixed to the rotary shaft of the third motor, and a linear motor fixed to the side of the holder, and the shaft of the linear motor may be connected to the placement portion so that the placement portion moves in an axial direction by means of the linear motor.

According to an embodiment of the present disclosure, an encoder may be mounted to the rotary shaft where the first link and the second link are hinged.

According to an embodiment of the present disclosure, a stereo camera for scanning the target for surgery may be mounted to the base.

As described above, the precise placement device according to the present disclosure allows an insert to be inserted at various angles.

In addition, since the precise placement device according to the present disclosure includes a planar transfer unit and a vertical transfer unit, which may rapidly transfer the insert to a set point, and a precise transfer unit, which may precisely transfer the insert, the time required for surgery may be shortened.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION

Hereinafter, an exemplary embodiment of a precise placement device according to the present disclosure will be described in detail with reference to the accompanying drawings.

Figure 1:
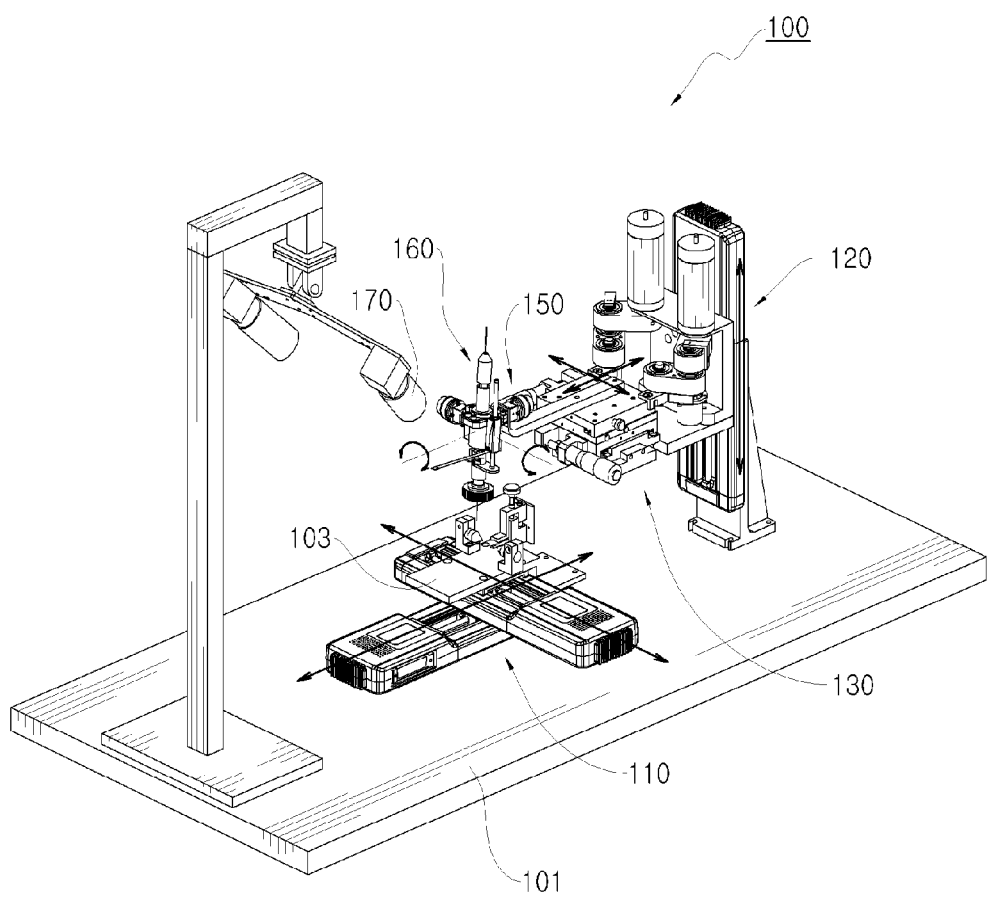
FIG. 1 is a perspective view showing a precise placement device according to an embodiment of the present disclosure.
Figure 2:
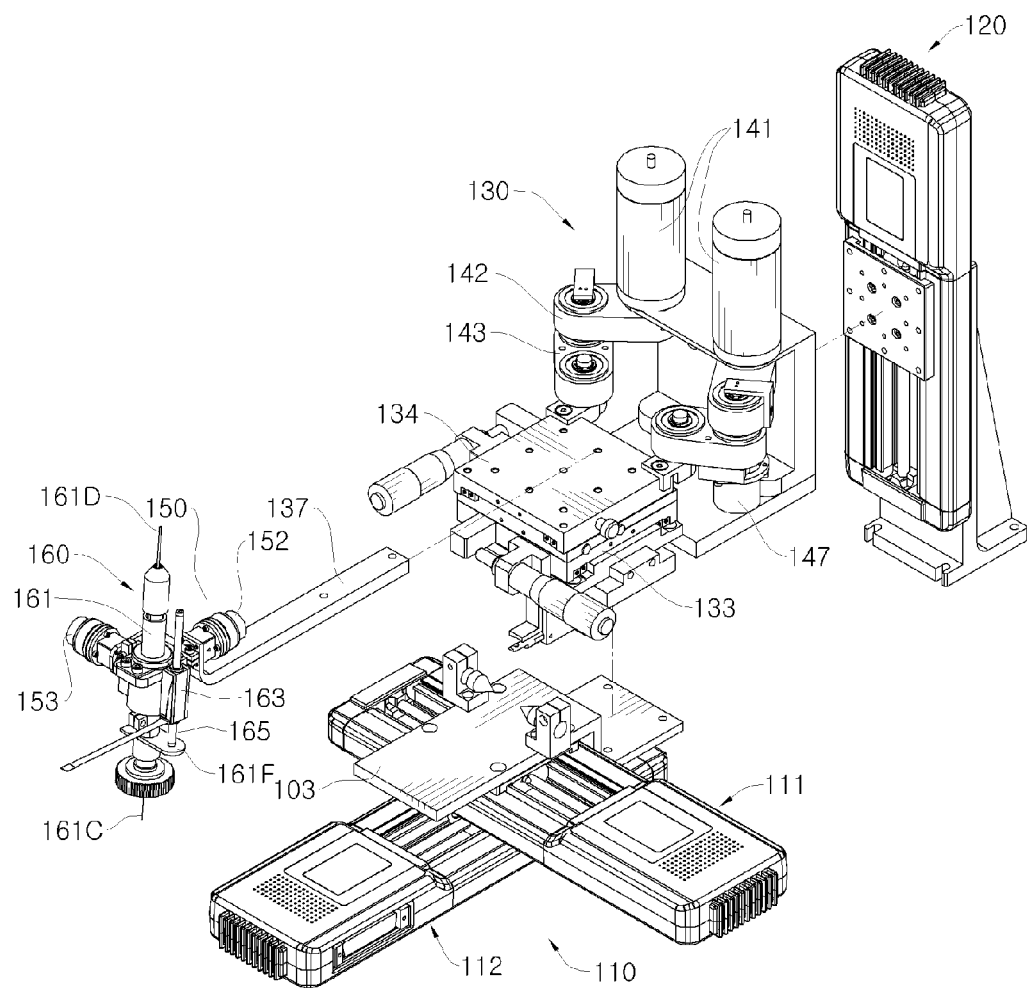
FIG. 2 is an exploded perspective view showing each essential operating portion of the precise placement device of FIG. 1.
Figure 3:
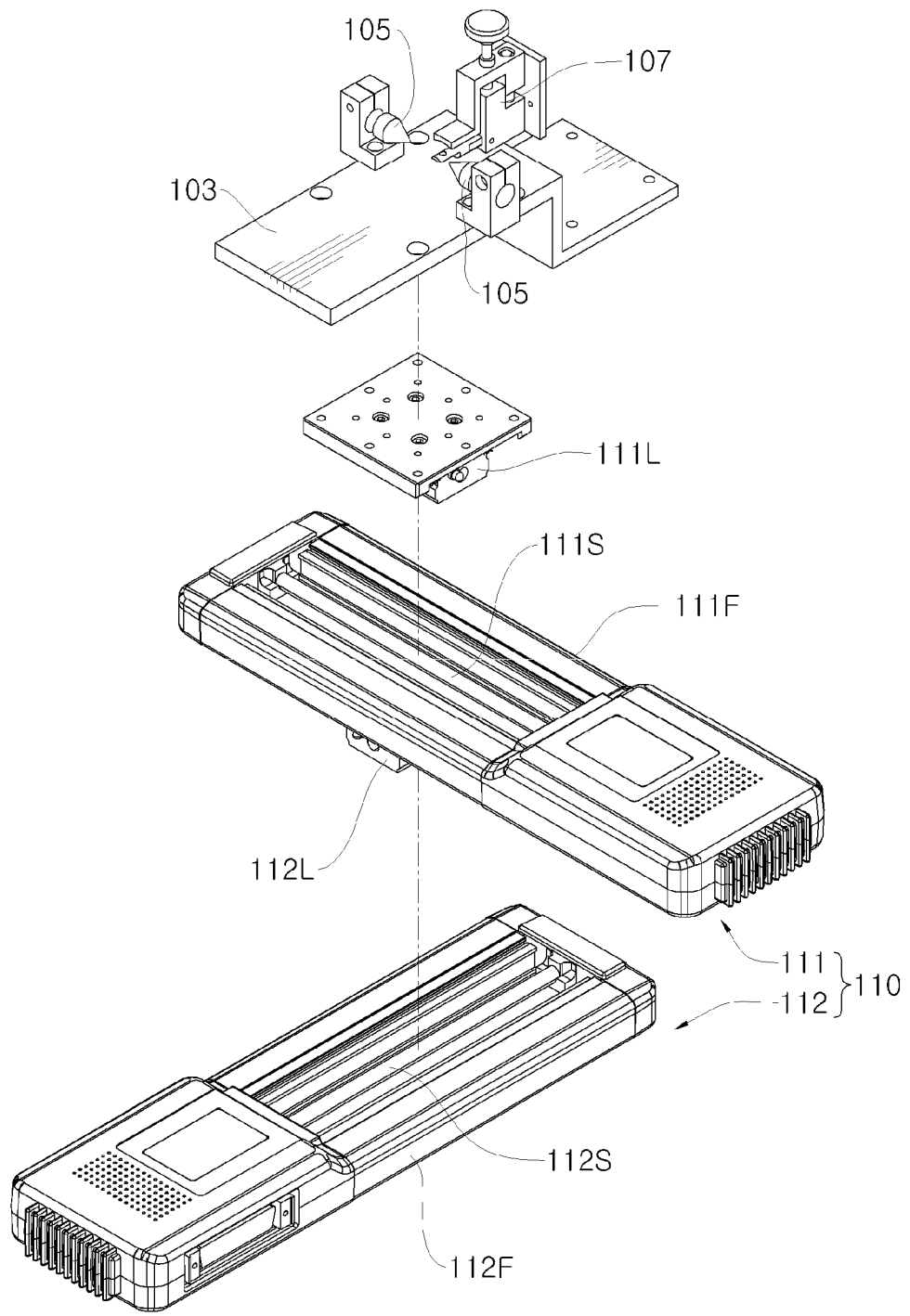
FIG. 3 is an exploded perspective view showing a planar transfer unit employed in the precise placement device of FIG. 2.
Figure 4:
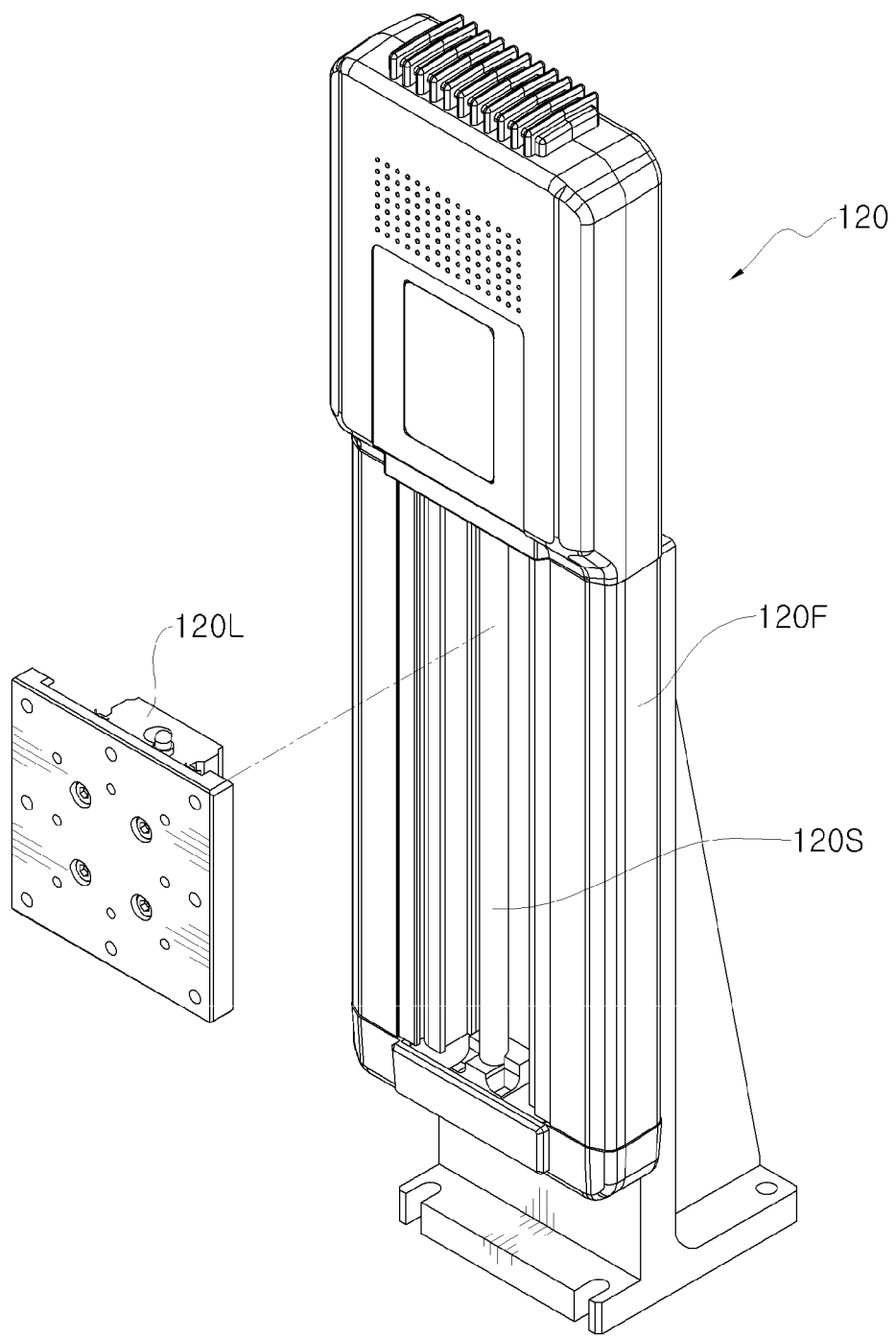
FIG. 4 is an exploded perspective view showing a vertical transfer unit employed in the precise placement device of FIG. 2.
Figure 5:
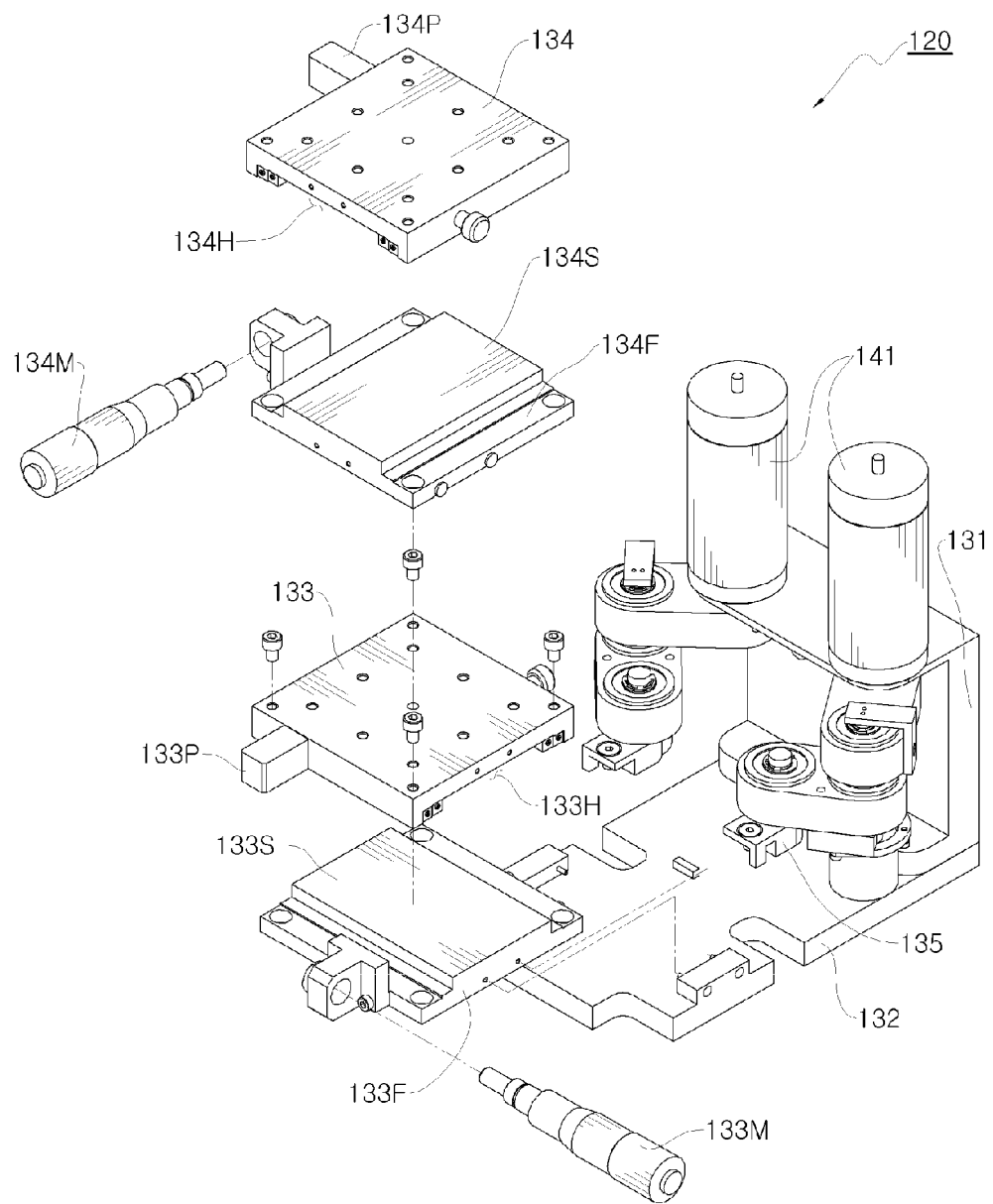
FIG. 5 is an exploded perspective view showing an operation portion of a precise transfer unit employed in the precise placement device of FIG. 2.
Figure 6:
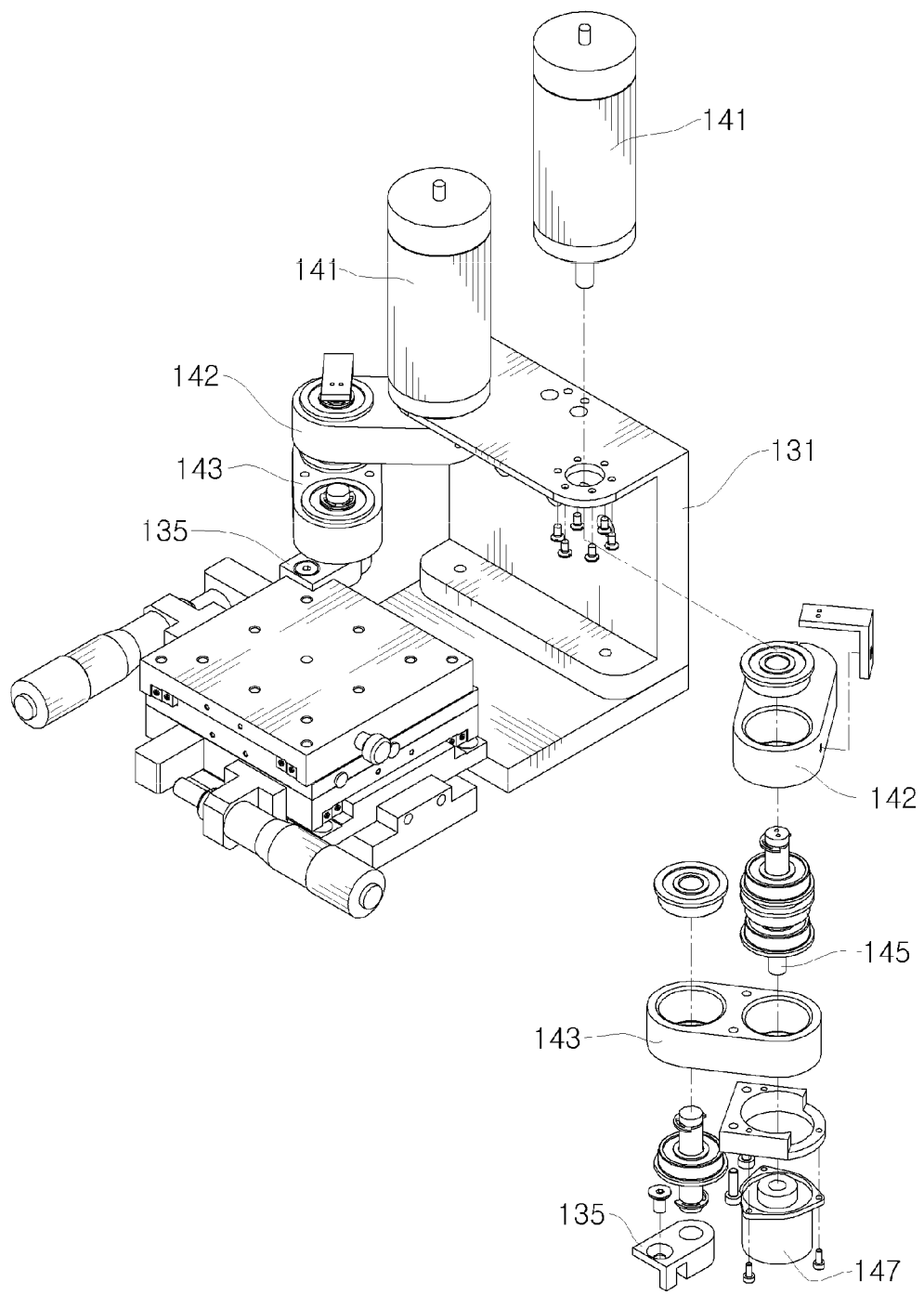
FIG. 6 is an exploded perspective view showing a driving portion of a precise transfer unit employed in the precise placement device of FIG. 2.
Figure 7:
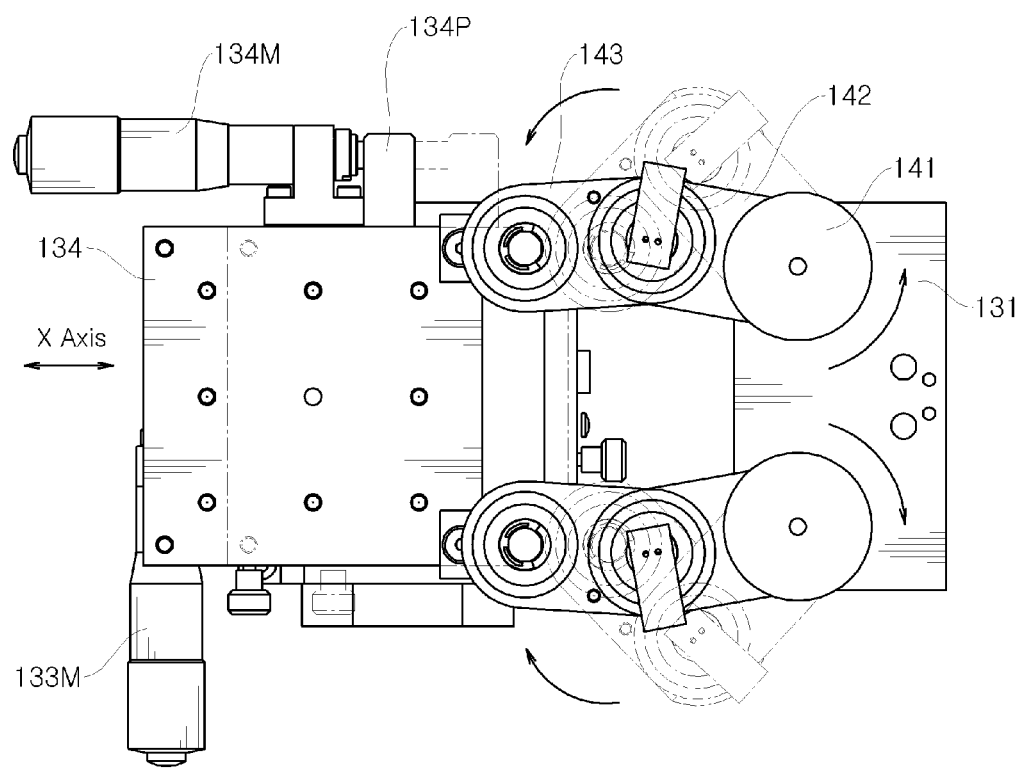
FIGS. 7 and 8 are diagrams for illustrating an operation relation of the precise transfer unit.
Figure 8:
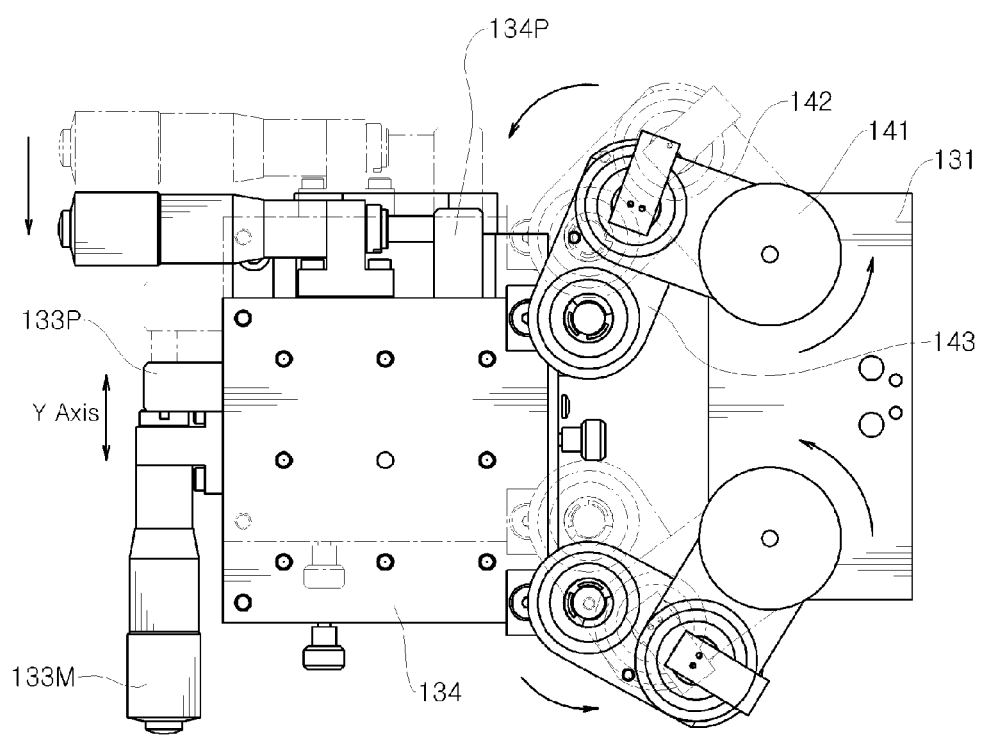
Figure 9:
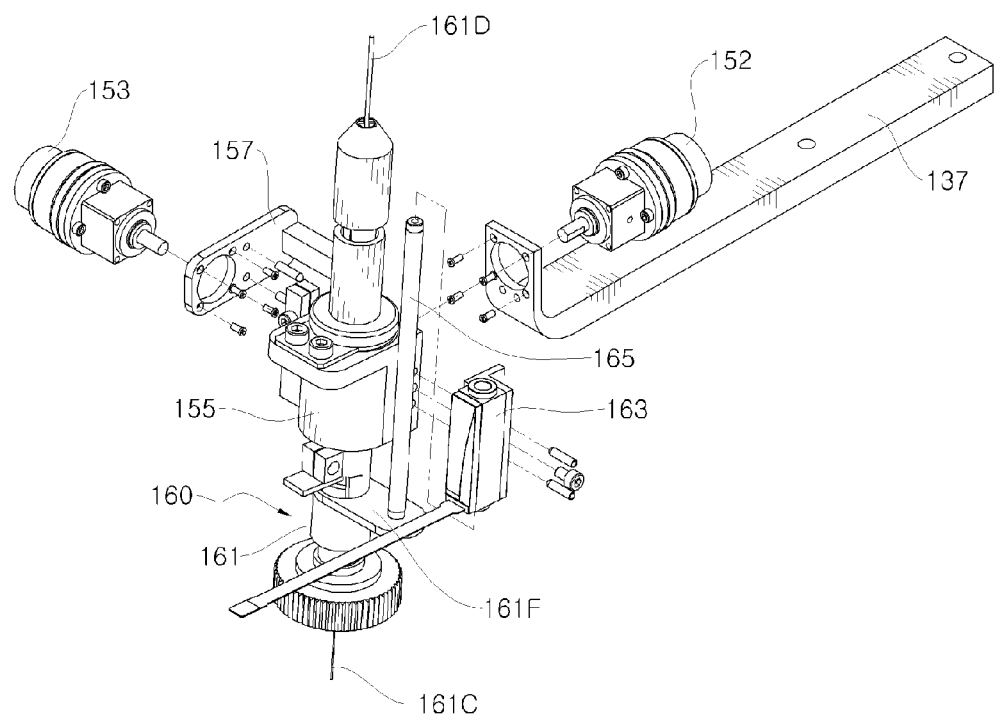
FIG. 9 is an exploded perspective view showing a direction controller and an electrode/drill placement portion employed in the precise placement device of FIG. 2.
Figure 10:
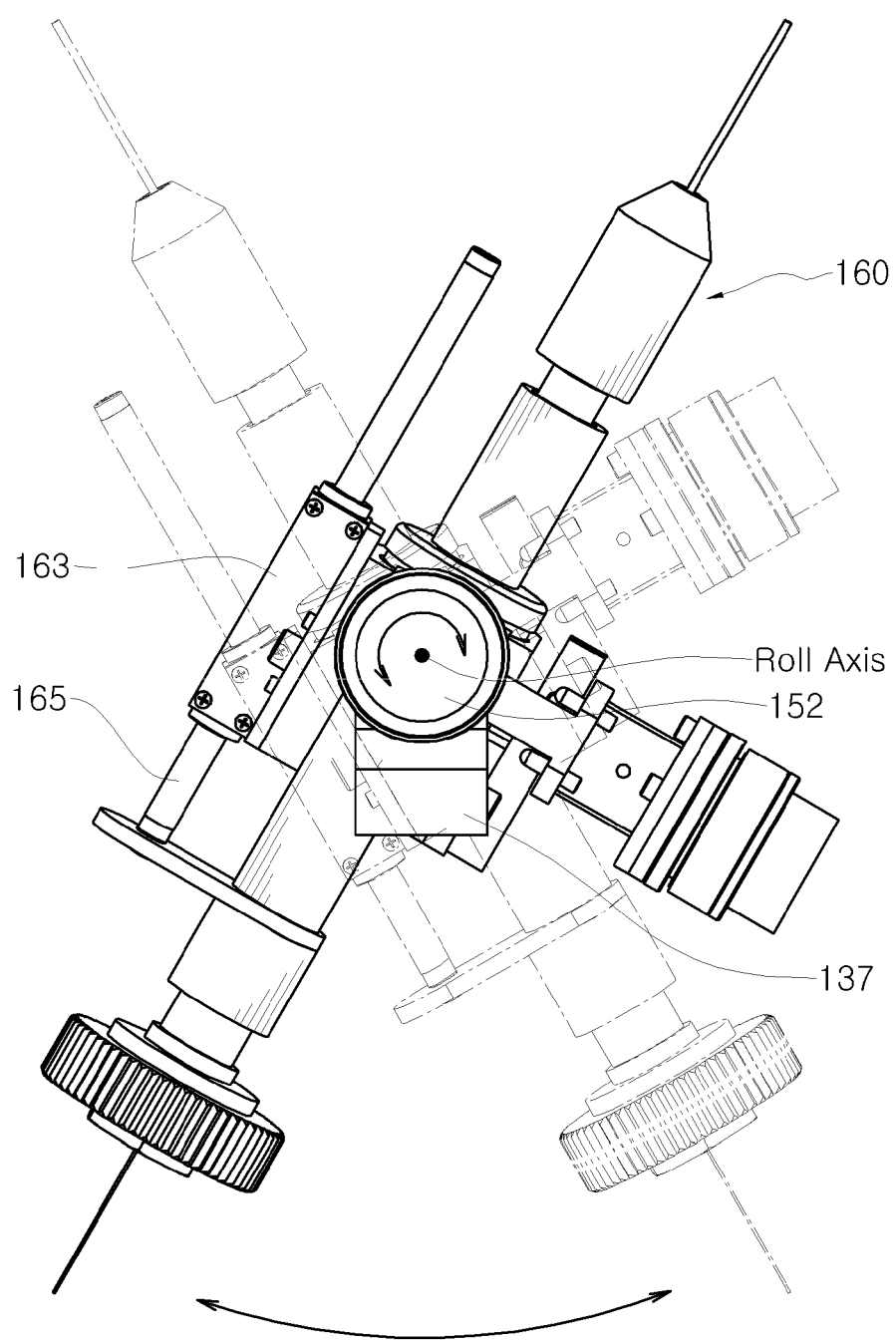
FIGS. 10 and 11 are perspective views for illustrating the electrode/drill placement portion which rotates based on a roll shaft and a pitch shaft by a direction controller.
Figure 11:
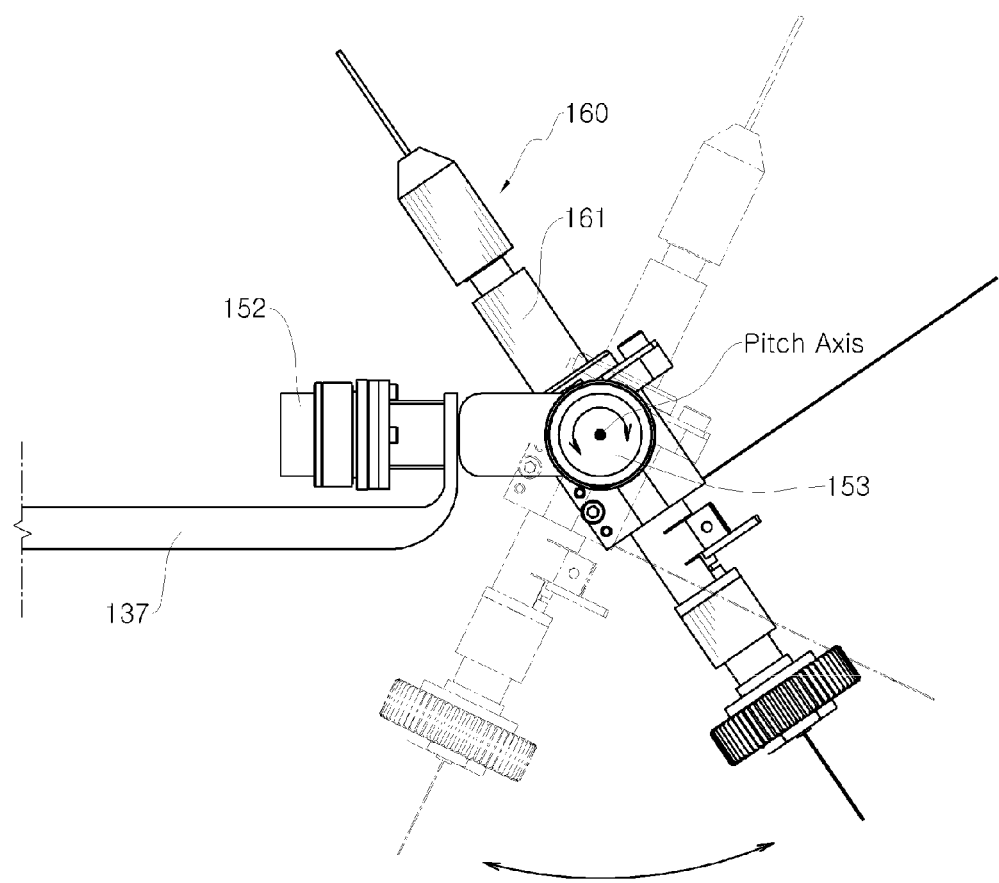

FIG. 1 is a perspective view showing a precise placement device for stereotactic surgery according to an embodiment of the present disclosure, FIG. 2 is an exploded perspective view showing each essential operating portion of the precise placement device of FIG. 1, FIG. 3 is an exploded perspective view showing a planar transfer unit employed in the precise placement device of FIG. 2, FIG. 4 is an exploded perspective view showing a vertical transfer unit employed in the precise placement device of FIG. 2, FIG. 5 is an exploded perspective view showing an operation portion of a precise transfer unit employed in the precise placement device of FIG. 2, FIG. 6 is an exploded perspective view showing a driving portion of a precise transfer unit employed in the precise placement device of FIG. 2, FIGS. 7 and 8 are diagrams for illustrating an operation relation of the precise transfer unit, FIG. 9 is an exploded perspective view showing a direction controller and an electrode/drill placement portion employed in the precise placement device of FIG. 2, and FIGS. 10 and 11 are perspective views for illustrating the electrode/drill placement portion which rotates based on a roll shaft and a pitch shaft by a direction controller.

Hereinafter, a precise placement device for stereotactic surgery of laboratory animals is described as an example of the precise placement device, but it should be understood that the use of the precise placement device according to the present disclosure is not limited thereto. For example, the precise placement device according to the present disclosure may also be used as a processing device for placing a machine processing article on a support table and precisely inserting a small object into a hole of the machine processing article perforated therein. In addition, the insert may be any small object which can be inserted into a hole formed by a drill, like a small tube.

As shown in FIGS. 1 and 2, a precise placement device 100 inserts an electrode into a target as an insert. Here, the target for insertion is an experimental rat. A support table 103 becomes an operating table at which an experimental rat is fixed for operation. The placement device includes a planar transfer unit 110 for transferring an operating table 103, at which an experimental rat is fixed, in planar 2-dimensional directions, a precise transfer unit 130 for precisely controlling a position of the electrode placement unit 160 mounted to a terminal thereof, a vertical transfer unit 120 to which the precise transfer unit 130 is mounted, the vertical transfer unit 120 transferring the precise transfer unit 130 in a vertical direction and, a direction controller 150 mounted to the terminal of the precise transfer unit 130 to control a direction of the electrode placement unit 160.

The electrode placement unit 160 is controlled to be positioned in a large region by the planar transfer unit 110 and the vertical transfer unit 120, controlled to be positioned in a precise region by the precise transfer unit 130, and controlled by the direction controller 150 to adjust its perforation angle and electrode placement angle.

Hereinafter, the precise placement device configured as above will be described in detail.

An experimental rat is placed on the operating table 103 and fixed to the operating table 103.

As shown in FIG. 3, components for fixing the cranial bone of the rat are mounted to the operating table 103. Particularly, ear holding portions 105 moving toward the ears of the rat are mounted at both sides of the operating table 103, and a clamp 107 for fixing the mouth of the rat is mounted at the front side of the operating table 103. Therefore, the rat placed on the operating table 103 is fixed by the ear holding portions 105 and the clamp 107 so that its head will not move. The ear holding portions 105 and the clamp 107 of the operating table 103 as described above are already commercially used in conventional electrode placement devices and not described in detail here.

The planar transfer unit 110 is mounted to the bottom surface of the operating table 103, and the planar transfer unit 110 transfers the operating table 103 on a plane along the X axis and the Y axis. Here, the axis connecting both ear holding portions 105 represents the Y axis, and the axis perpendicular to the Y axis on the plane represents the X axis.

A Y-axis transfer portion 111 is mounted to the bottom surface of the operating table 103 and transfers the operating table 103 in the Y-axis direction, and an X-axis transfer portion 112 is mounted to the bottom surface of the Y-axis transfer portion 111 to transfer the Y-axis transfer portion 111 in the X-axis direction. In addition, the bottom surface of the X-axis transfer portion 112 is fixed to a base 101. Therefore, the operating table 103 is movable in the X-axis and Y-axis directions by the X-axis transfer portion 112 and the Y-axis transfer portion 111 of the planar transfer unit 110.

The X-axis transfer portion 112 and the Y-axis transfer portion 111 as well as a vertical transfer unit 120, described later, include frames 111F, 112F, 120F, having one open end, shafts 111S, 112S, 120S fixed to the inside of the open end in the length direction of the frames 111F, 112F, 120F, and linear motors 111L, 112L, 120L coupled to the shafts 111S, 112S, 120S to move in the length direction of the shafts 111S, 112S, 120S, as shown in FIGS. 3 and 4, and each moving body moving in the axis of each transfer unit is mounted to each linear motor.

In other words, the frame 112F of the X-axis transfer portion 112 is fixed to the base 101, a frame 111F of the Y-axis transfer portion 111 is fixed to the linear motor 112L of the X-axis transfer portion 112, and the operating table 103 is fixed to the linear motor 111L of the Y-axis transfer portion 111, so that the operating table 103 may be movable along the X axis and the Y axis.

As shown in FIG. 4, the vertical transfer unit 120 is perpendicularly fixed to the base 101 at the front of the operating table 103. The frame 120F of the vertical transfer unit 120 is perpendicularly fixed to the base 101 by means of a bracket, and the linear motor 120L of the vertical transfer unit 120 moves in the length direction of the shaft 120S (Z axis) fixed to the frame 120F. The precise transfer unit 130 is mounted to the linear motor 120L of the vertical transfer unit 120.

Therefore, the experimental rat moves along the X axis and the Y axis by means of the planar transfer unit 110, and the electrode placement unit 160 moves along the Z axis by means of the vertical transfer unit 120. The planar transfer unit 110 and the vertical transfer unit 120 are used to control a position of the electrode placement unit 160 and transfer the electrode placement unit 160 with the degree of precision of 1 mm to a relatively larger region in comparison to the precise transfer unit 130 with the degree of precision of 50 μm, described below. In this embodiment, the precision of 1 mm and 50 μm are just examples.

According to this embodiment, the planar transfer unit 110 and the vertical transfer unit 120 move a great distance at a high speed to transfer the electrode placement unit 160, and the precise transfer unit 130 moves a relatively short distance at a low speed to move the planar transfer unit 110 and the vertical transfer unit 120 with very high precision so that the electrode placement unit 160 is precisely transferred.

The precise transfer unit 130 precisely transfers the electrode placement unit 160 in the planar two-axis (X-axis and Y-axis) directions.

As shown in FIG. 5, the precise transfer unit 130 includes a fixed bracket 131 fixed to the linear motor 120L of the vertical transfer unit 120, a horizontal bracket 132 fixed to the bottom surface of the fixed bracket 131, a Y-axis plate 133 moving in the Y-axis direction with respect to the horizontal bracket 132, and an X-axis plate 134 mounted to the upper surface of the Y-axis plate 133 to move in the X-axis direction. The fixed board 137 is fixed to the upper surface of the X-axis plate 134, and the electrode placement unit 160 is mounted to the terminal of the fixed board 137. In addition, as shown in FIG. 6, a pair of first driving motors 141 is perpendicularly mounted to the fixed bracket 131, and one end of a first link 142 is fixed to the rotary shaft of the first driving motor 141. In addition, one end of a second link 143 is hinged to the other end of the first link 142 to be relatively rotatable thereto, and one end of the second link 143 is hinged to a bracket 135 fixed to the X-axis plate 134.

In the precise transfer unit 130 configured as above, as shown in FIG. 7, in a case where one pair of first driving motors 141 rotate in opposite directions, the first link 142 pivots to increase or decrease a gap, and the second link 143 rotatably mounted to the other end of the first link 142 also pivots accordingly to pull or push the X-axis plate 134 in the X-axis direction. Meanwhile, as shown in FIG. 8, in a case where one pair of first driving motors 141 rotate in the same direction, the X-axis plate 134 connected to the second link 143 moves in the Y-axis direction. At this time, the X-axis plate 134 moves in the Y-axis direction due to the movement of the Y-axis plate 133 without movement on the X-axis coordinate.

Hereinafter, the precise transfer unit 130 will be described in more detail.

A Y-axis fixed plate 133F is fixed to the upper surface of the horizontal bracket 132, a protrusion 133S is formed at the upper surface of the Y-axis fixed plate 133F in the Y-axis direction, and a groove 133H matched with the protrusion 133S is formed at the bottom surface of the Y-axis plate 133. Therefore, the Y-axis plate 133 moves in the length direction (Y-axis) of the protrusion 133S formed at the Y-axis fixed plate 133F due to the operation of the first driving motor 141. In addition, a micrometer 133M is fixed to the side of the Y-axis fixed plate 133F, and a rod of the micrometer 133M is fixed to a protrusion 133P protruding to the side of the Y-axis plate 133. Therefore, the micrometer 133M measures a moving distance of the Y-axis plate 133 in the Y-axis direction.

An X-axis fixed plate 134F is fixed to the upper surface of the Y-axis plate 133. A protrusion 134S in the X-axis direction is formed at the upper surface of the X-axis fixed plate 134F, and a groove 134H matched with the protrusion 134S is formed at the bottom surface of the X-axis plate 134. Therefore, the X-axis plate 134 moves in the length direction (X-axis) of the protrusion 134S formed at the X-axis fixed plate 134F due to the operation of the first driving motor 141. In addition, a micrometer 134M is fixed to the side of the X-axis fixed plate 134F, and a rod of the micrometer 134M is fixed to a protrusion 134P extruding to the side of the X-axis plate 134. Therefore, the micrometer 134M measures a moving distance of the X-axis plate 134 in the X-axis direction.

As described above, two micrometers measure a moving distance of the X-axis plate 134 along the X axis and a moving distance of the Y-axis plate 133 along the Y axis, and an encoder 147 is rotatably mounted to a rotary shaft 145 which connects the first link 142 and the second link 143 to measure a rotating angle of the second link 143.

The precise transfer unit 130 configured as above controls positions of the X-axis plate 134 and the Y-axis plate 133 to the degree of precision of 50 μm due to the operation of the first driving motor 141.

The fixed board 137 is fixed to the upper surface of the X-axis plate 134, the direction controller 150 is mounted to the terminal of the fixed board 137, and the electrode placement unit 160 mounted to the direction controller 150 is controlled by the direction controller 150 to adjust its direction.

Hereinafter, the direction controller and the electrode placement unit will be described in more detail.

As shown in FIG. 9, a second driving motor 152 is fixed to the terminal of the fixed board 137, and one end of an L-type bracket 157 is fixed to the rotary shaft (roll shaft) of the second driving motor 152. In addition, a third driving motor 153 is fixed to the other end of the L-type bracket 157, and a holder 155 is fixed to the rotary shaft (pitch shaft) of the third driving motor 153. An electrode/drill placement portion 161 of the electrode placement unit 160 is inserted into and placed in the hollow formed in the holder 155. Therefore, the electrode/drill placement portion 161 may move in the length direction of the hollow in a state of being interposed into the hollow of the holder 155. In addition, a linear motor 163 is mounted to the side of the holder 155, and the shaft 165 of the linear motor 163 is fixed to a fixture 161F fixed to the side of the electrode/drill placement portion 161. A drill 161D is mounted to one side of the electrode/drill placement portion 161, and an electrode 161C is mounted to the other side thereof. Due to the operation of the linear motor 163, the electrode/drill placement portion 161 makes linear movement.

Therefore, as shown in FIGS. 10 and 11, the electrode/drill placement portion 161 of the electrode placement unit 160 rotates based on the roll shaft by means of the second driving motor 152 and rotates based on the pitch shaft by means of the third driving motor 153. Accordingly, the electrode/drill placement portion 161 is controlled to be oriented toward the perforation point of the incised cranial bone of the rat by using the second driving motor 152 and the third driving motor 153, and the drill 161D perforates at the perforation point and then is extracted. In addition, the electrode/drill placement portion 161 is rotated by 180 degrees by means of the second driving motor 152 and then the electrode 161C is placed into the perforated hole.

A stereo camera 170 for scanning the cranial bone of the rat fixed to the operating table 103 is mounted to the base 101.

Hereinafter, the operation of the precise placement device configured as above will be described.

In order to insert an electrode into the cranial bone of a rat by using the precise placement device 100, first, the rat is fixed to the operating table 103, the scalp is incised so that the cranial bone of the rat is exposed, and then the cranial bone is scanned by the stereo camera 170. In addition, after the placement point of the electrode is set, the precise placement device is operated according to a programmed order or manual work of the user.

In order to move the electrode/drill placement portion 161 to a placement point of the electrode, primarily, the planar transfer unit 110 and the vertical transfer unit 120 having the degree of precision of 1 mm are operated. As the planar transfer unit 110 and the vertical transfer unit 120 operate, the electrode/drill placement portion 161 and the rat move, and the electrode/drill placement portion 161 rapidly move near the electrode placement position set at the rat. In addition, the first driving motor 141 is operated to precisely control location in the X-axis and Y-axis directions, and the second driving motor 152 and the third driving motor 153 are operated to rotate the electrode/drill placement portion 161 based on the roll shaft and the pitch shaft so that the drill 161D is precisely controlled to be oriented toward the nerve nucleus at the electrode placement position.

In addition, the linear motor 163 is operated to perforate by the drill 161D of the electrode/drill placement portion 161, and the electrode/drill placement portion 161 is moved back to extract the drill 161D out of the cranial bone. After that, the second driving motor 152 is operated to control a position of the electrode/drill placement portion 161 so that the electrode 161C is oriented toward the perforated hole, and the linear motor 163 is operated to insert the electrode 161C through the perforated hole to the nerve nucleus. After the electrode 161C is placed in the nerve nucleus, the precise placement device is returned back to the original position in a reverse order.

In the precise placement device configured and operated as above, the linear motor of the transfer units may be modified into a mechanical mechanism which converts the rotation of the motor into linear movement. For example, the linear motor may be replaced with a screw rotated by a motor and a nut block coupled to the screw, or it may also be easily modified by using a mechanical mechanism of a rack and a pinion.

While the exemplary embodiments have been shown and described, it will be understood by those skilled in the art that various changes in form and details may be made thereto without departing from the spirit and scope of the present disclosure as defined by the appended claims.

What is claimed is:

1. A precise placement device, comprising:
a direction controller to which a placement unit having an insert and a drill is mounted, the direction controller configured to control a direction of the placement unit;
a precise transfer unit to which the direction controller is mounted, the precise transfer unit configured to transfer the placement unit in planar two-axis directions;
a support table for fixing a target in which the insert is to be placed; and
macro transfer units configured to transfer the precise transfer unit and the support table,
wherein the macro transfer units comprise a planar transfer unit, the planar transfer unit comprising:
an X-axis transfer portion including a first frame fixed to a base, a first shaft fixed to the frame in a first direction, and a first linear motor moving along the first shaft, and
a Y-axis transfer portion including a second frame mounted to the first linear motor of the X-axis transfer portion, a second shaft fixed to the second frame in a second direction, and a second linear motor moving along the second shaft.

2. The precise placement device according to claim 1, wherein the macro transfer units include a vertical transfer unit to which the precise transfer unit is mounted, the vertical transfer unit configured to transfer the precise transfer unit in a vertical direction.

3. The precise placement device according to claim 2, wherein the vertical transfer unit includes a frame perpendicularly fixed to a base, a shaft fixed to the frame in the vertical direction orthogonal to the planar two-axis directions, and a third linear motor moving along the shaft, and wherein the precise transfer unit is mounted to the third linear motor.

4. The precise placement device according to claim 2, wherein the precise transfer unit includes two plates mounted to the vertical transfer unit configured to relatively move in a first direction and a second direction orthogonal to the first direction, and two first motors each linked to one of the two plates, respectively, the first motors configured to relatively move the plates in the first and the second directions.

5. The precise placement device according to claim 4, wherein:
a first fixed plate having a protrusion in one of the first and the second directions is fixed to a bracket horizontally fixed to the vertical transfer unit,
a first plate matched with the protrusion, and configured to move along the protrusion is mounted to an upper surface of the first fixed plate,
a second fixed plate having a protrusion in the other of the first and the second directions is fixed to the upper surface of the first plate,
a second plate matched with the protrusion of the second fixed plate, and configured to move along the protrusion is mounted to an upper surface of the second fixed plate, and a link and the direction controller are mounted to the second plate.

6. The precise placement device according to claim 5, wherein:
a bracket is fixed to one end of the second plate so that the link is hinged to the bracket, and a fixed board is fixed to the other end of the second plate so that the direction controller is mounted to a terminal of the fixed board.

7. The precise placement device according to claim 4, wherein the two first motors are mounted to a bracket fixed to the vertical transfer unit, one end of a first link is fixed to a rotary shaft of each of the two first motors, one end of a second link is hinged to the other end of the first link, and the other end of the second link is hinged to the plate.

8. The precise placement device according to claim 7, wherein an encoder is mounted to the rotary shaft where the first link and the second link are hinged.

9. The precise placement device according to claim 1, wherein the X-axis transfer portion is configured to transfer the support table in the first direction and the Y-axis transfer portion is configured to transfer the support table in the second direction, and
wherein the support table is fixed to the second linear motor.

10. The precise placement device according to claim 1, wherein the direction controller includes a second motor mounted to the precise transfer unit, a bracket fixed to a rotary shaft (roll shaft) of the second motor to rotate based on the rotary shaft of the second motor, and a third motor fixed to the bracket, and
wherein the placement unit is fixed to a rotary shaft (pitch shaft) of the third motor to rotate based on the rotary shaft of the third motor, the placement unit being rotatable based on the rotary shaft (roll shaft) of the second motor.

11. The precise placement device according to claim 10, wherein the placement unit includes a placement portion having one end to which the drill is mounted and the other end to which the insert is mounted, and a holder having a hollow through which the placement portion passes and fixed to the rotary shaft of the third motor, and a linear motor fixed to the side of the holder, and
wherein the shaft of the linear motor is connected to the placement portion so that the placement portion moves in an axial direction by means of the linear motor.

12. The precise placement device according to claim 10, wherein the placement unit includes a placement portion having one end to which the drill is mounted and the other end to which an electrode is mounted, a holder having a hollow through which the placement portion passes and fixed to the rotary shaft of the third motor, and a linear motor fixed to the side of the holder.

13. The precise placement device according to claim 1, wherein a stereo camera for scanning the target for insertion is mounted to the base.

14. The precise placement device according to claim 1, wherein the precise placement device is an electrode placing device for stereotactic surgery,
wherein the insert is an electrode, and
wherein the support table is an operating table at which a target for operation is fixed.

15. A precise placement device of claim 1, wherein the direction controller is further configured to control a perforation angle and placement angle for the insert, the drill or both.

* * * * *